United States Patent [19]

Gray et al.

[11] Patent Number: 4,517,547

[45] Date of Patent: May 14, 1985

[54] WATER-IN-FUEL SENSOR CIRCUIT AND METHOD

[75] Inventors: Randall C. Gray, Scottsdale; W. Eric Main, Mesa, both of Ariz.

[73] Assignee: Motorola, Inc., Chicago, Ill.

[21] Appl. No.: 323,643

[22] Filed: Nov. 20, 1981

[51] Int. Cl.³ .............................................. B60Q 1/00
[52] U.S. Cl. ................................. 340/59; 73/304 C; 324/61 P; 324/60 CD
[58] Field of Search .................. 340/870.37, 59, 620; 324/60 CD, 61 P, 59; 73/304 C

[56] References Cited

U.S. PATENT DOCUMENTS

| | | | |
|---|---|---|---|
| 3,947,760 | 3/1976 | Noguchi | 324/60 CD |
| 4,001,676 | 1/1977 | Hile | 324/60 CD |
| 4,090,408 | 5/1978 | Hedrick | 73/304 C |
| 4,103,225 | 7/1978 | Stephens | 324/60 CD |
| 4,193,063 | 3/1980 | Hitt | 340/870.37 |
| 4,316,174 | 2/1982 | Sutton | 340/59 |
| 4,339,750 | 7/1982 | Delacruz | 324/60 CD |

*Primary Examiner*—James J. Groody
*Attorney, Agent, or Firm*—Michael D. Bingham

[57] ABSTRACT

A reference capacitor is coupled in parallel with a capacitor of which the size thereof is variable and an oscillator is used to alternately charge and discharge both capacitors between first and second voltage levels. The absolute magnitude of the current flowing through the reference capacitor, which varies in proportion to the size of the variable capacitor, is detected which is indicative of the variations in size of the variable capacitor. If the variable capacitor is disposed in the fuel tank of a vehicle, water in the fuel will cause the effective capacitance value of the capacitor to increase which reduces the absolute magnitude of the current that is detected. The absolute magnitude of the detected current can be utilized to indicate excessive water levels in the fuel.

22 Claims, 4 Drawing Figures

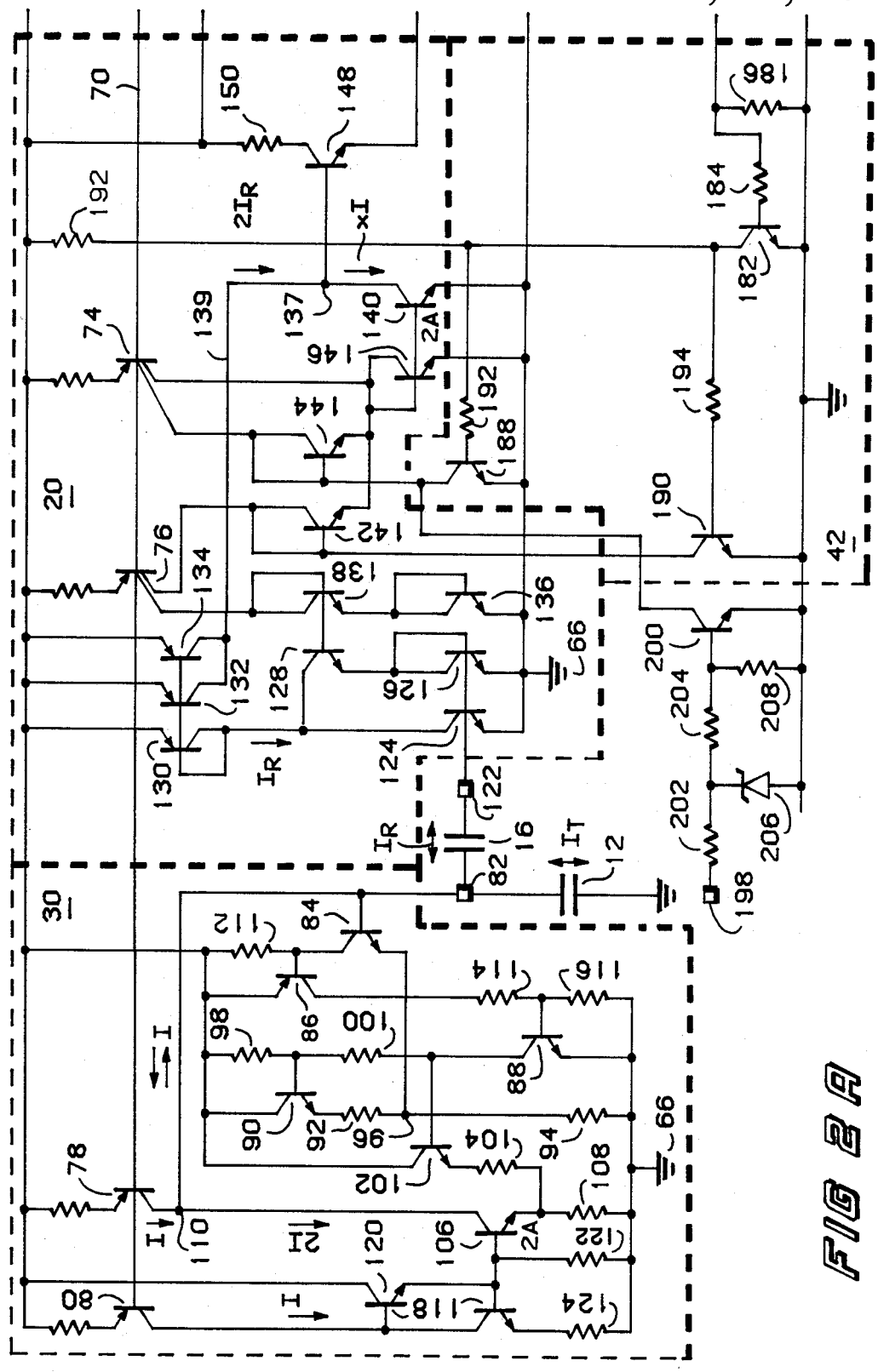

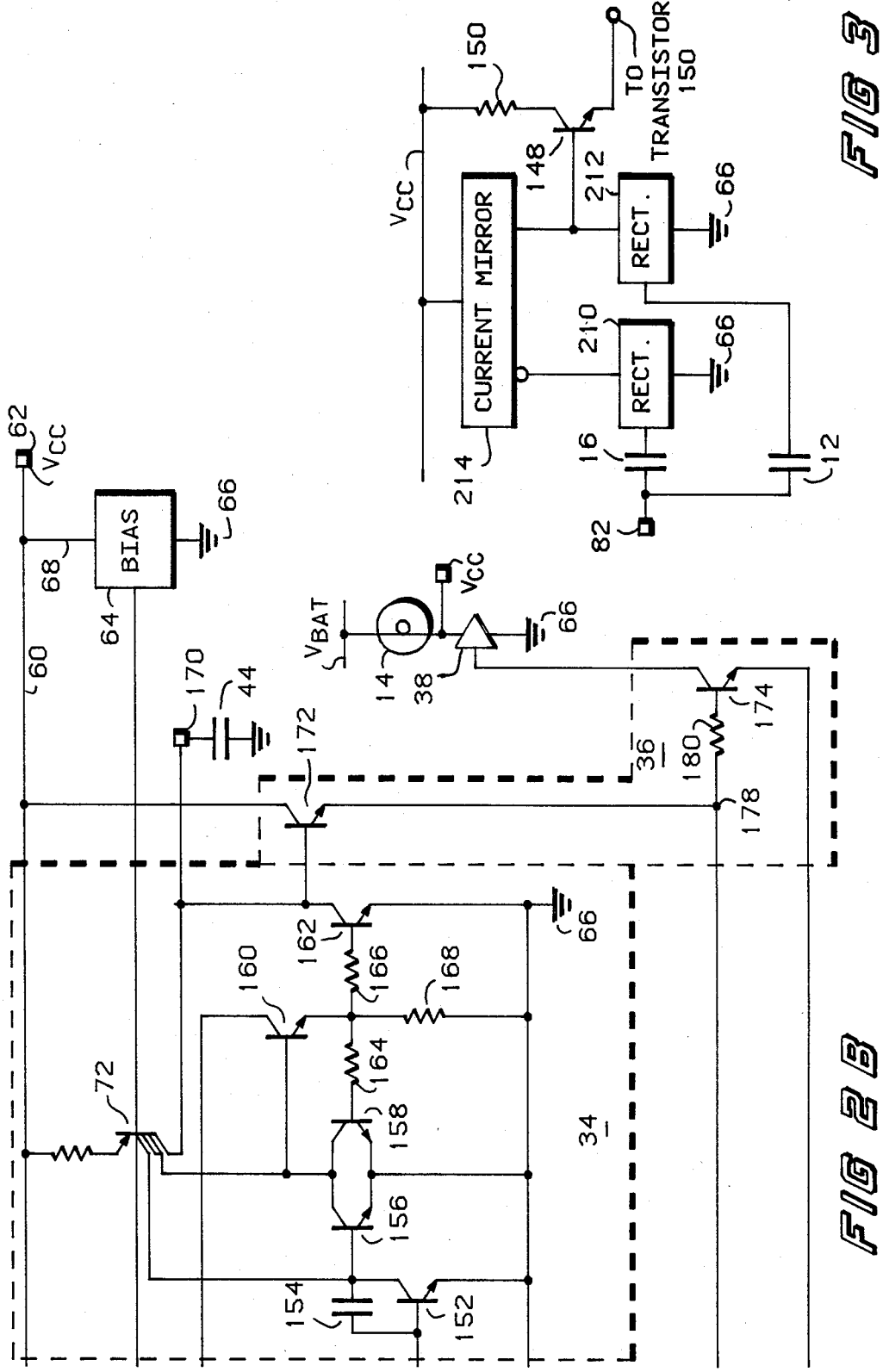

WATER-IN-FUEL SENSOR CIRCUIT AND METHOD

BACKGROUND OF THE INVENTION

1. Field of the Invention

This invention relates to a circuit for sensing the change in capacitance of variable capacitor and, more particularly, to a sensor circuit for detecting excessive amounts of water in the fuel tank of a vehicle by sensing the capacitance change of a probe capacitor positioned within the fuel tank.

2. Description of the Prior Art

In attempt to conserve the earth's limited reserve of fossil fuel, many automotive manufacturers are increasingly building more and more automobiles that are driven by diesel fuel supplied internal combustion engines. Diesel engines are generally more fuel efficient than relatively sized gasoline operated engines. A problem related more to diesel engines arises if water is allowed to accumulate in the diesel fuel. Due to the nature of the diesel engine, water in the fuel can damage or even destroy the fuel pump, fuel system and or fuel injectors of the diesel engine.

Until recently diesel engines were mainly used only in commercial vehicles such as earth moving equipment, buses, etc. and very expensive automobiles. Because of the expensive nature of these vehicles, complex and expensive filter systems could be utilized to inhibit water from getting into the diesel fuel. However, as diesel engines are now being used in massed produced consumer oriented automobiles, the automotive manufacturers are in need of a simple and reliable sensor circuit that can detect excessive amounts of water in the fuel such that the operator can be alerted to this condition.

Generally, it is desired to have a dash mounted panel light that can be lit up on the dash panel of the vehicle to warn the operator of water in the fuel tank. The operator would as soon as possible thereafter have the fuel tank drained to remove the excess water.

It is generally known that water can be differentiated from the diesel fuel by its dielectric constant. Since water does not homogeneously mix with the fuel but rather goes to the bottom of the fuel tank, it's presence can be determined by utilizing a capacitor which varies in value as water is displaced thereabout and comparing it's value to a reference capacitor. In fact, at least one automobile manufacturer uses such a scheme for detecting water in the fuel. Basically, this prior art scheme uses an oscillator to regularly charge up both capacitors while allowing the capacitors to discharge through fixed value resistors while at the same time comparing the voltages developed there across. Water causes an increase in the capacitor size of the variable capacitor and thus the voltage developed thereacross which eventually will cause the output of the comparator to go positive at a predetermined point. This output is then rectified and filtered to be used to turn on a warning lamp.

Several problems are associated with this prior art system. The system is relatively expensive, utilizing building block integrated circuits in combination with discrete devices. Additionally, the system suffers in its accuracy. Hence, a need exists for such a system which is suitable to be manufactured in integrated circuit form to reduce system cost while increasing system accuracy.

SUMMARY OF THE INVENTION

Accordingly, it is an object of the present invention to provide an improved sensing circuit for detecting variations in the capacitance of a capacitor.

Another object of the present invention is to provide an improved Water-In-Fuel Sensor Circuit for detecting excessive water levels in fuel.

Still another object of the present object is to provide a method for sensing variations in the capacitance of a capacitor.

In accordance with the above and other objects there is provided an improved sensing circuit for detecting the change in capacitance of a variable capacitor, which includes a reference capacitor that is coupled essentially in parallel with the variable capacitor. An oscillator is used to alternately charge and discharge both capacitors between first and second voltage levels. The resulting current through the reference capacitor varies in magnitude as the size of the variable capacitor varies. The absolute magnitude of this current is detected and compared with a known current wherein the difference current therebetween is indicative of the variations in the capacitor size of the variable capacitor.

One feature of the present invention is that the sensing circuit is suited to be fabricated in integrated circuit form to which the variable capacitor and reference capacitor are then connected. The sensing circuit is utilized to detect excessive water in the fuel of a vehicle. As the water content increases, the capacitance of the variable capacitor increases thereby reducing the magnitude of the rectified current. As the magnitude of the rectified current decreases below the magnitude of the known current the sensing current produces a useful output signal that may be utilized to turn on a warning lamp.

BRIEF DESCRIPTION OF THE DRAWINGS

FIGS. 2A and 2B are detailed schematics illustrating the sensing circuit of the preferred embodiment of the present invention; and FIG. 3 is a partial block and schematic diagram illustrating a particular embodiment of the detector circuit of the present invention.

DETAILED DESCRIPTION OF THE PREFERRED EMBODIMENT

Figure 1:
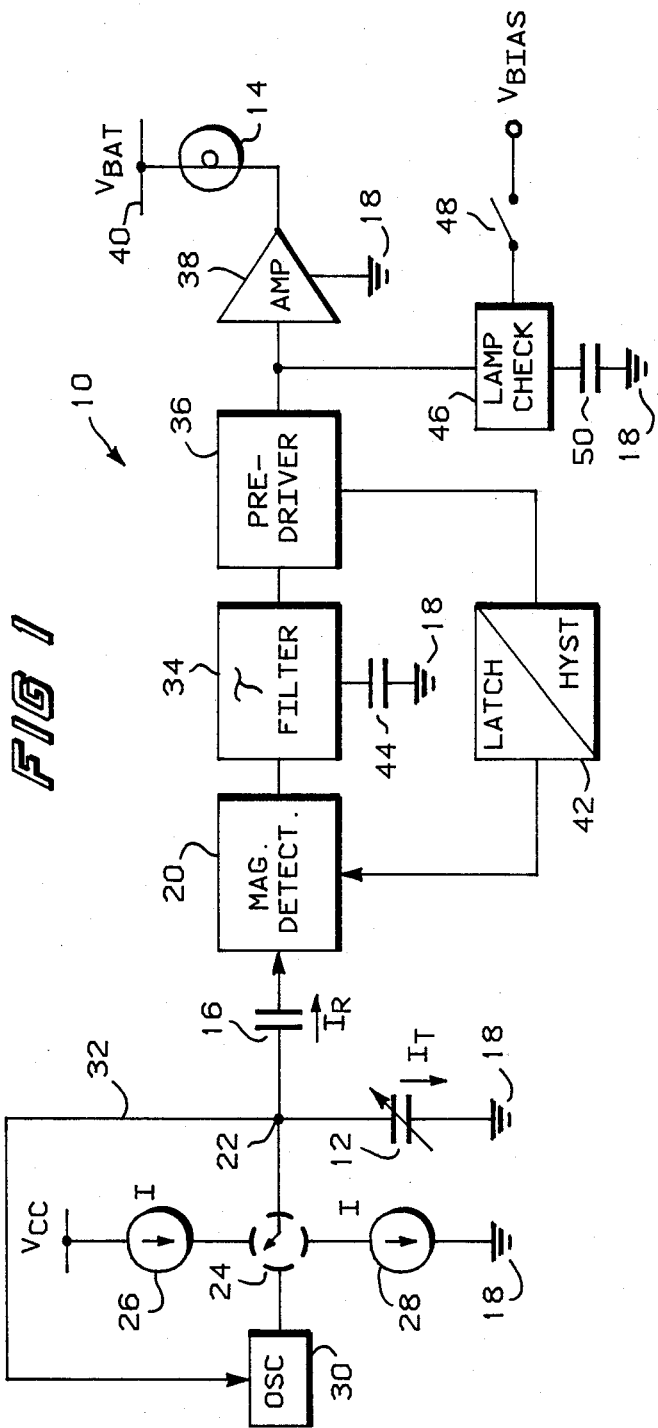
FIG. 1 is a partial block diagram in a schematic illustrating the sensing circuit of the present invention.

Turning now to FIG. 1, there is illustrated sensor circuit 10 of the present invention in general block diagram form. Sensor circuit 10 detects changes in the capacitance value of capacitor 12, which may be a transducer or probe type capacitor element for instance. Thus, capacitor 12 could be utilized to provide an indication of the environment in which it is placed. For example, capacitor 12 may be a probe type capacitor that is situated in the fuel tank of an internal combustion engine driven vehicle to detect the presence of water in the fuel. Such probes are available and have been used by the automotive industry in the past wherein the capacitance of the probe increases or decreases as the water content increases or decreases. Hence, if as shown in FIG. 1, capacitor 12 is coupled to sensor circuit 10, a warning light 14, that is situated on the dash panel of the vehicle, could be lit to indicate that a harmful amount of water content is in the fuel as capacitor 12 increases in value above a predetermined value. In response, the vehicle operator would be alerted to immediately having the fuel tank drained which prevents excessive water in the fuel from damaging the fuel pump and fuel injectors of a diesel type combustion engine for example.

The manner in which sensor circuit 10 detects the capacitance change in capacitor 12 is now briefly explained. A known current I is shared between probe capacitor 12 and a reference capacitor 16. Capacitor 12 is referenced to a ground reference potential while capacitor 16 is referenced to a virtual ground potential through detector circuit 20 such that these two capacitors, which are commonly coupled at node 22, are essentially placed in parallel configuration with respect to each other. The known current I is either sourced to or from node 22 as controlled switch 24 is either connected to current source 26 or 28 respectively. The charge on the capacitor 12 and capacitor 16 is limited by the supply voltage $V_{CC}$ so that the polarity of the current I is regularly reversed by the action of oscillator 30 controlling switch 24 in conjunction with receiving a feedback signal via lead 32 from node 22. Hence capacitor 12 and capacitor 16 are alternately charged and discharged between first and second voltage levels. The value of the current $I_T$ that flows through capacitor 12 is a function of the capacitance value of this capacitor and can be determined from the known value of I and the current $I_R$ which flows through fixed reference capacitor 16. Thus, $I_T$ is equal to:

$$I_T = I - I_R \tag{1}$$

and;

$$\frac{I_R}{I_T} = \frac{C_{16}}{C_{12}} \tag{2}$$

therefore;

$$I_R = \frac{C_{16}}{C_{16} + C_{12}} \tag{3}$$

As shown above, the value of the reference current $I_R$ is proportional to the variation in capacitance $C_{12}$ of capacitor 12 wherein the capacitance $C_{16}$ of reference capacitor 16 is fixed.

Magnitude detector 20 includes a full wave rectifier circuit which rectifies the current $I_R$. The rectified current, which is equal to the absolute magnitude of the current $I_R$, is supplied to a comparator circuit included within detector circuit 20. The rectified current is then compared by the comparator circuit to a current of known and predetermined value, xI, which may be, as indicated, proportional to the total current I. The value of the proportionality factor, x, is fixed and is made equal to:

$$x = \frac{C_{16}}{C_{16} + C_{12}} \tag{4}$$

Too much water in the fuel is therefore indicated when the absolute magnitude of the current IR becomes less than the value or xI which causes the output of the comparator circuit to trip or change output level states. The changing of output state of the comparator is utilized then to turn on lamp 14 to warn the operator of this condition. In response, the operator would have the fuel drained from the fuel tank to prevent damage to the fuel system of the vehicle.

Although not specifically shown, it is considered apparent that in a general application variable capacitor 12 and reference capacitor 16 could be interchanged wherein the magnitude of current through the variable capacitor is directly detected and compared with the known current. The circuit would function as aforedescribed.

Although not necessary to the present invention as described above, sensor circuit 10 may include a delay filter 34 and an amplifying circuit comprising predriver amplifier 36 and output amplifier 38. A time delay through circuit 34 is made to be substantially equal to one cycle of operation of sensor circuit 10 to thereby inhibit tripping of the system due to transient signals caused by inherent differences between the magnitudes of the charging and discharging currents I as generated from oscillator 30. Hence, the sensor circuit operates off the larger magnitude of current I which is measured continuously by detector circuit 20. Predriver amplifier 36 amplifies the output from filter 34 to provide an input to amplifier 38 which in turn provides sufficient current to turn on lamp 14 as current flows therethrough between battery supply 40 and ground reference. Also included is latch/hysteresis circuit 42 which is coupled between predriver 36 and detector circuit 20.

As the amount of water in the fuel becomes excessive (IR<xI) the output of the comparator circuit of detector circuit 20 is caused to change output states and delay filter capacitor 44 is allowed to charge up from ground reference. Capacitor 44 continues to charge until the voltage developed thereacross exceeds a predetermined value which thereafter renders predriver 36 operative. Latch circuit 42 is rendered operative in response to predriver 36 becoming operative to increase the current, xI, by a predetermined value which introduces hysteresis into the circuit by increasing the trip point at which the comparator circuit will change output states. Thus, sensor circuit 10 is latched into an on condition to maintain the warning lamp 14 turned on.

A lamp check circuit 46 may also be provided that is rendered operative as ignition switch 48 of the vehicle is closed to light up lamp 14 for a predetermined interval whereby the operator knows that lamp 14 is functional. The lamp check circuit 46 remains operative until capacitor 50 is charged to a predetermined voltage level which renders the circuit nonoperative to then turn off lamp 14.

Turning now to FIG. 2 there is shown sensor circuit 10 in more detail. Circuit 10 of FIG. 2 is suited to be manufactured in integrated circuit form except for the three external capacitors 12, 16 and 44. Power supply conductor 60 is connected at external coupling pad 62 to a source of operating potential, $V_{CC}$, which is supplied to sensor circuit 10. The operating potential may be obtained from the battery voltage as shown in FIG. 2B. A master bias circuit 64 is coupled between supply conductor 60 and ground reference potential 66 to provide a master bias voltage potential between terminal 68 and 70 for biasing the plurality of PNP current sourcing transistor 72, 74, 76, 78 and 80. Master bias circuit 64 is a circuit that may generally be well known to those skilled in the art. The current sourcing transistors each have a respective degeneration resistor coupled in the emitter paths thereof as understood and may be either single or multi-collector output devices as shown.

Capacitor 12, which may be a probe type capacitor, is coupled between the output of oscillator 30 (at external connecting pad 82) and ground reference potential 66. In the preferred embodiment probe capacitor 12 would be situated in the fuel tank of a vehicle. Oscillator 30 both sources current to and sinks current from pad 82 of substantially equal magnitudes which charges and discharges capacitor 12 and capacitor 16 between first and second voltage levels. Thus, assuming no charge across capacitor 12, transistors 84, 86 and 88 are in a non-conductive state. Hence, transistor 90 is conducting which places a bias potential at the connection of resistors 92 and 94, at node 96, which insures that transistor 84 is turned off. Similarly, with transistor 88 being off, a bias potential is developed at the interconnection of series connected resistors 98 and 100 to maintain transistor 102 conductive. Because the emitter of transistor 102 is connected via resistor 104 to the emitter of transistor 106 to be returned to ground reference through resistor 108, a bias potential is set up on the emitter of transistor 106 which reverse biases this transistor into a non-conducting state. In this state of operation, a current of magnitude I is supplied from the collector of current sourcing transistor 78 to node 110 directly to pad 82 for charging capacitors 12 and 16 which are connected at this node. Capacitor 12 and 16 are caused to be charged by the current I until such time that the voltage at pad 82, and hence at the base of transistor 84, becomes sufficient to overcome the back bias voltage maintain at the emitter of this transistor as supplied from node 96. When this occurs, transistor 84 is rendered conductive which establishes a bias current through resistor 112. Thereafter, transistor 86 is rendered conductive as base current is supplied through transistor 84. This action causes transistor 102 to become non-conductive as all available base drive current thereto is now sourced through the collector-emitter path of transistor 88. As transistor 102 is turned off the reverse bias voltage at the emitter transistor 106 is removed.

Transistors 118, 120 and 106 are connected in a well known current mirror configuration such that the current of magnitude I supplied to the collector of transistor 118 from current sourcing transistor 80 is mirrored in the collector of transistor 106. As indicated, the emitter area of transistor 106 is made twice (2A) the size of the emitter area of transistor 118 such that the collector current of transistor 106 is made equal to 2I. Because transistor 78 can only supply a current of magnitude I, transistor 106 causes capacitors 12 and 16 to be discharged at proportional rates to supply the additional current I. Therefore, as was previously described, oscillator 30 alternately sources a current I to and then from pad 82. Transistor 106 will remain conductive until such time that the voltage level appearing at node 82 decreases to a first level voltage which renders transistor 84 non-conductive to allow transistor 102 to become conductive thereby repeating the aforedescribed cycle.

Referenced capacitor 16 is connected between pad 82 and external pad 122 to the input of magnitude detector circuit 20. Detector circuit 20 includes a full wave current rectifier circuit comprising transistors 124, 126, 128, 130, 132 and 134. Diode connected transistors 136 and 138 which are coupled between ground reference to the collector-emitter path of transistor 76 set the bias to transistor 128 and thus to the input transistors 124 and 126. The full wave rectifier is known in the art such that the operation thereof is only briefly described hereinafter.

As a current IR is sourced to the input of the full wave rectifier, to the bases of transistors 124 and diode-connected transistor 126, the current at the collector of transistor 124 will be equal to IR and is sourced through diode connected transistor 130. Transistors 130, 132 and 136 are connected as a typical current turn around mirror circuit such that a current of magnitude 2IR is sourced to node 137 via lead 139. Similarly, as a current IR is sourced from the full wave rectifier through output pad 122, an equal magnitude current flows through the collector-emitter path of transistor 128 which also produces a current of 2IR to node 137. Thus, in response to the current IR that is alternately sourced to and from pad 122 (as capacitor 16 is charged and discharged) a rectified current of magnitude 2IR is continuously sourced to node 137. The magnitude of the rectified current maybe made any value and may be equal to IR. In the present embodiment the magnitude of the rectified current was doubled with respect to the current flowing through reference capacitor 16 in order to overcome any parasitic capacitance which may appear at the collector of transistor 140 due to the nature of the structure of this transistor in integrated circuit form. It should be also noted that as transistors 124 and 126 have their respective emitters connected to ground reference 66 reference capacitor 16 is placed essentially at a virtual ground reference. Thus, the two capacitors 12 and 16 are placed in substantially parallel configuration.

In the preferred embodiment, probe capacitor 12 is made such that it extends into the fuel tank whereby it is normally surrounded by fuel. However, water, either by fuel contamination or condensation, occurring in the fuel tank will go to the bottom thereof to surround capacitor 12. The dielectric constant of water, being different from the fuel, causes the effective capacitance of capacitor 12 to increase from its nominal value: the greater the percentage of water in the fuel the greater is the magnitude of the effective capacitance of the probe capacitor. This variation of the magnitude of the effective capacitance $C_{12}$ with increasing percentages of water in the fuel can be empirically determined. Thus, from equation 4, a value x can be predetermined which is indicative of an excessive amount of water in the fuel and at which warning lamp 14 is to be turned on.

In view of the above, because the value of the current IR is proportional to the capacitance $C_{12}$ (see equation 3) and the total current I, the magnitude of current 2IR supplied to node 137 can be compared with a fixed reference current xI to turn on lamp 14 when ever the value of the current 2IR becomes less than the current xI: the trip point of the aforementioned comparator. The manner in which this comparison is carried out is by sinking the current xI from node 137 through the collector-emitter path of transistor 140. Sufficient base current drive is supplied to the base of transistor 140 to cause a collector current of magnitude xI to flow therethrough between node 137 and ground reference via the collector-emitter path of this transistor. Base current drive to transistor 140 is supplied via current sourcing transistors 74 and 76 which have respective collectors connected to diode connected transistors 142, 144, and 146. As illustrated, diode-connected transistors 142, and 144 have there emitters commonly connected to the base-collector electrodes of transistor 146, the emitter of which is connected to the base of transistor 140, thereby forming a current mirror circuit.

In normal operation, with no water or with insufficient amounts of water in the fuel to be of concern, the value of the current 2IR sourced to node 137 exceeds the value of the current xI. Transistor 148, which has its collector coupled via resistor 150 to power supply conductor 60, acts as the output of the comparator circuit and sources current to the base of transistor 152: the base of transistor 152 being coupled to the emitter of transistor 148. If, however, excessive water appears in the fuel the value of the current 2IR at node 137 becomes less than the current xI that transistor 140 wants to sink. This state will cause transistor 148 to become nonconductive as there is no longer sufficient base current drive available thereto. Thus, a current proportional to the current flowing through capacitor 12, which itself is proportional to the magnitude of current flowing through probe capacitor 12, is compared with a known current (xI) to cause switching of the output of the comparator transistor 148 whenever an excessive amount of water occurs in the fuel of the vehicle.

The input of delay filter circuit 34 is taken at the base of transistor 152. A capacitor 154 is coupled between the base and collector of transistor 152 which produces an effective capacitance at the emitter of transistor 148 to ground reference that is equal to the beta amplification factor of transistor 152 times the value of the capacitor 154. This effective capacitor filters switching transient signals that otherwise could occur as transistor 148 is switched between a conducting and non-conducting state. Transistor 152 and capacitor 154 act as an active filter having a delay period greater than one cycle of operation to thereby inhibit false switching at the trip point which might otherwise occur because the value of the current I that charges capacitors 12 and 16 is not equal to the current I that discharges these same capacitors. By providing filtering, the changing of states of transistor 148 is dependent only on the relative size of capacitor 12 to capacitor 16 and is not dependent on any differences in the magnitude of the charging and discharging currents supplied to or from pad 82.

As aforementioned, with little or no water in the fuel, transistors 148 and 152 are conductive: collector current to transistor 152 being provided by current sourcing transistor 72 having a respective collector coupled to the collector of transistor 152. Base current drive to transistor 156 is therefore inhibited as transistor 152 sinks all the current from the collector of transistor 72 connected thereto to ground via the collector-emitter path thereof. Hence, transistor 156, which has its collector and emitter connected with in parallel with the collector and emitter of transistor 158 is turned off. Transistor 158 which is connected as a well known current mirror circuit in combination with transistors 160, 162, and resistors 164, 166, and 168, is turned on as transistor 156 is turned off to cause transistors 160, and 162 to become conductive whereby all of the current source from multiple-collector transistor 72 to these transistors is shunted to ground reference. Therefor, transistor 162 holds the plate of capacitor 44 that is coupled at pad 170 essentially at ground reference to maintain transistor 172 in an non-conductive state.

Transistor 172, which forms with transistor 174 the predriver circuit 36 and which in combination the aforementioned current mirror circuit may be considered an output circuit, inhibits conduction of transistor 174 as no base current drive is supplied thereto. Amplifier 38 which has its input coupled to the collector of transistor 174 is therefor maintained in an non-conductive state. Hence, with no water in the fuel, lamp 14 remains off. However, as transistor 148 is turned off due to excessive water in the fuel, transistor 156 will be turned on to turn off transistor 158 of the aforementioned current mirror. Consequently, transistor 162 is also turned off. This allows capacitor 44 to begin charging towards $V_{CC}$. When the voltage across capacitor 44 exceeds the turn on voltage of transistor 172 this transistor is rendered conductive to source current through is collector-emitter path to node 178. Transistor 174 which has its base coupled to node 178 through resistor 180 is therefore turned on to then turn on amplifier 38. This causes lamp 14 to be lit.

Prior to lamp 14 being turned on, in response to transistor 172 being rendered conductive, transistor 182 is rendered conductive by transistor 172 since the base of this transistor is coupled to node 178 via resistor 184. Resistor 186 is coupled between the emitter of transistor 172 and ground reference for biasing purposes. Thus, base current drive is stolen from respective transistors 188 and 190, each having the base thereof coupled to the collector of transistor 182 via resistors 192 and 194 respectively. Therefore, as all of the available current from power supply conductor 60 via resistor 196 is now sourced through the collector-emitter path of transistor 182 these two transistors are turned off. As transistors 188 and 190 are rendered non-conductive, more current is allowed to be supplied via diode-connected transistors 142 and 144 to transistor 146. This in turn increases the base current supplied to transistor 140 to provide a hysteresis action whereby the trip point at which transistor 148 is to be shut off is raised high enough to latch sensor circuit 10 into a conducting state that after once sensing excessive water in the fuel will cause lamp 14 to remain on until the water is removed. In fact, the trip point is sufficiently high so that even if the effective value of capacitor $C_{12}$ is reduced to zero, the system will not revert back to it's normal operating mode until latch circuit 42 is disabled by a latch disabling signal supplied to pad 198.

If a latch disabling signal is applied to pad 198, transistor 200 is turned on as it's base is coupled via resistors 202 and 204 to pad 198. As a transistor 200 is rendered conductive, sufficient latch current is sinked to ground through the collector-emitter path of transistor 200 that is coupled between the collector of transistor 188 and ground reference to allow transistor 140 to be driven by a modified trip point base drive current. This introduces hysteresis into the circuit until such time that the water level content is reduced to a minimum allowable percentage. Thereafter, transistor 190 would be rendered non-conductive. Hence, the collector current of transistor 140 is reduced to the original trip point value (xI). Now, because there is no longer excessive water in the fuel, the value of current 2IR is sufficient to turn on transistor 148 and consequently to turn off transistor 172. Lamp 14 is then turned off and normal operation of the sensor circuit is resumed. Zener diode 206 which is coupled between the interconnection of resistors 202 and 204 and ground reference provides over voltage protection to transistor 200. Resistor 208 is provided as a bias resistor and is coupled between the emitter and the base of transistor 200.

Turning to FIG. 3, there is shown a modified portion of detector circuit 20 which would allow detecting the currents through both capacitors 12 and 16 and sensing the difference directly therebetween. In this embodiment, reference capacitor 16 is coupled to a rectifier section 210 as previously discussed. Additionally, probe or variable capacitor 12 would have the electrode previously connected to ground reference connected to the input of additional rectifier section 212. Rectifier section 212 is identical to rectifier 210 and is shown in FIG. 2A comprising transistors 124, 126, 128, 136, 138 and current sourcing transistor 76. Current turn around and mirror circuit comprising transistors 130, 132 and 134 could be replaced with current mirror circuit 214 of similar construction wherein the current flowing from the input (indicated by the half circle) thereof, due to the current flowing through capacitor 16, appears at the output which is coupled to the base of transistor 148. This current is then directly compared with the current flowing through capacitor 12 as the output of rectifier 212 is connected to the output of current mirror 214. The current sourced at the output of rectifier 212 is directly proportional to the current flowing through capacitor 12. Thus, the difference current between the respective currents flowing through capacitors 12 and 16, which is proportional to the size of capacitor 16, can be used to switch the operating state of comparator transistor 148 as described above.

Thus, what has been described above, is a novel sensor circuit which in the preferred embodiment may by utilized for sensing excessive water in the fuel of a diesel fuel operated internal combustion engine. The sensor circuit is suited to be fabricated in integrated circuit form to reduce system cost while increasing the accuracy of the system.

What is claimed is:

1. A sensing circuit for detecting a change in the capacitance of a variable capacitor, comprising:
   a first capacitor having a substantially constant and predetermined value, said first capacitor being connected at a first circuit node essentially in parallel with the variable capacitor;
   means coupled to said first circuit node for alternately sourcing a substantially constant current to and then from said first circuit node;
   detector circuit means operative coupled to said first capacitor for detecting the absolute magnitude of the current flowing through said first capacitor as said first capacitor is alternately charged and then discharged by a portion of said current sourced to and from said first circuit node flowing therethrough and comparing said detected current to a current of predetermined and substantially constant magnitude, said current flowing through said first capacitor varying in magnitude as the capacitance of the variable capacitor varies such that the difference current between said detected current and said current of predetermined magnitude is indicative of the variation in the capacitance value of the variable capacitor.

2. The sensing circuit of claim 1 wherein said means for alternately sourcing a current to and from said first and variable capacitors includes an oscillator circuit, said oscillator circuit producing a charging and discharging current of substantially equal value as said first capacitor and the variable capacitor are charged and discharged between first and second voltage levels.

3. The sensing circuit of claim 2 wherein said detector circuit means includes:
   a full wave rectifier circuit having an input coupled with said first capacitor and an output for producing a rectified current at said output in response to said first capacitor being linearly charged and discharged between said first and second voltage levels; and
   current mirror means for establishing said current of predetermined and substantially constant magnitude said current mirror means having an output coupled with said output of said full wave rectifier thereby sinking a portion of said rectified current up to an amount equal to the magnitude of said current of predetermined magnitude; and
   comparator means having an input coupled with said outputs of said full wave rectifier and said current mirror means and an output, said output of said comparator means being caused to be switched between first and second output level states as the magnitude of said rectified current exceeds or decreases below the magnitude of said current of predetermined and substantially constant magnitude respectively.

4. The sensing circuit of claim 3 including:
   filter means coupled to said output of said comparator means for inhibiting switching transent signals as said comparator means is caused to be switched between output level states; and
   output circuit means coupled to an output of said filter means which is responsive to said comparator means switching from said first output level state to said second output level state for producing an output signal at an output thereof a predetermined time interval thereafter.

5. The sensing circuit of claim 4 including:
   latch circuit means coupled between said output of said output circuit means and said current mirror means which is responsive to said output signal for causing the magnitude of said current established by said current mirror means to increase wherein the sensing circuit is latched into its then existing state of operation; and
   disabling circuit means operatively coupled to said latch circuit means which is responsive to a latch disable signal supplied thereto for disabling said latch circuit means wherein said current established by said current mirror means is returned to an intermediate predetermined magnitude level.

6. The sensing circuit of claim 5 including:
   a lamp coupled at one electrode thereof to a source of operating potential; and
   amplifying means having an input coupled to said output of said output circuit means and an output coupled with a second electrode of said lamp, said amplifying means being responsive to said output signal for causing a current to flow through said lamp whereby said lamp is lit as the capacitance of the variable capacitor exceeds a predetermined value.

7. A monolithic integrated sensor circuit suitable for detecting a capacitance change in a variable capacitor coupled thereto, the sensor circuit being adapted to receive an operating potential supplied thereto, comprising:
   a first capacitor of predetermined value, said first capacitor being coupled to the sensor circuit at first and second terminals thereof and being connected essentially in parallel with the variable capacitor, the variable capacitor being connected at one electrode to said first terminal of the sensing circuit, the other electrode of which is referenced to a ground reference potential;
   circuit means having an output coupled to said first terminal for alternately sourcing a current to said first terminal and then sinking a current there from to charge and discharge said first capacitor and the variable capacitor between first and second voltage levels, the magnitude of current flowing through said first capacitor being proportional to the capacitance value of the variable capacitor; and detector circuit means having an input coupled to said second terminal for detecting the absolute magnitude of said current flowing through said first capacitor and for comparing said detected current to a current of predetermined and substantially constant magnitude wherein the difference current therebetween is indicative of the capacitance value of the variable capacitor.

8. The sensing circuit of claim 7 wherein said circuit means including an oscillator circuit which is responsive to the voltage at said first terminal being less than or equal to said first voltage level for sourcing a current, I, to said first terminal and being responsive to the voltage at said first terminal rising to said second voltage level for sinking a current, I, therefrom until the voltage at said first terminal decreases to said first voltage level.

9. The sensing circuit of claims 8 wherein said detector circuit means includes:
a full wave rectifier circuit coupled to said second terminal for producing a rectified current at an output thereof which is directly proportional to the magnitude of said current flowing through said first capacitor;
current mirror means for establishing said current of predetermined and substantially constant magnitude, said current mirror means having an output coupled with said output of said full wave rectifier circuit wherein said rectified current is sourced by said current mirror means up to the value of said predetermined magnitude; and
comparator means coupled to said outputs of said full wave rectifier circuit and said current mirror means which is responsive to the value of said rectified current exceeding the value of said current of predetermined and substantially constant magnitude for causing the output thereof to switch from a first output level state to a second output level state.

10. The sensing circuit of claim 9 including:
filter means coupled to said output of said comparator means for inhibiting switching transient signals whenever the output of said comparator means switches between said output level states; and
output circuit means coupled with an output of said filter means which is responsive to said output of said comparator means switching to said second output level state for producing an output signal a predetermined time interval thereafter.

11. The sensing circuit of claim 10 including:
latch circuit means coupled between said output of said output circuit means and said current mirror means which is responsive to said output signal for causing the magnitude of said current of predetermined magnitude to increase wherein the sensing circuit is latched into its existing state of operation; and
disabling means responsive to a disable signal supplied thereto and which is operatively coupled with said latch circuit means for disabling said latch circuit means wherein said current established by said current mirror means is reduced to an intermediate predetermined magnitude.

12. The sensing circuit of claim 11 including:

a lamp, having first and second electrodes, said first electrode being coupled to the operating potential; and
amplifying means having an input coupled to said output of said output circuit means and an output coupled to said second electrode of said lamp, said amplifying means being responsive to said output signal for causing current to flow through said lamp thereby lighting the same whenever the capacitance of the variable capacitor exceeds a predetermined value.

13. In a vehicle having an internal combustion engine, a fuel tank and fuel supply system for operating the engine, a water-in-fuel sensor circuit, comprising:
a first capacitor disposed in said fuel tank wherein the capacitance value thereof varies as water is displaced thereabouts, the capacitance being caused to vary from a minimum to a maximum value in response to the level of water in the fuel tank increasing from a nominal value to an excessive level;
a second capacitor of predetermined value, said second capacitor being connected essentially in parallel to said first capacitor externally of the fuel tank;
circuit means for alternately and linearly charging and discharging said first and second capacitors between first and second voltage levels, the magnitude of current flowing through said second capacitor varying as said first capacitor varies in capacitive value; and
detector circuit means for detecting the absolute magnitude of said current flowing in said second capacitor and for comparing a current proportional to said detected current to an additionaly current of predetermined magnitude to provide an output signal whenever the magnitude of said current flowing in said second capacitor decreases below a predetermined value which is indicative of excessive water levels in the fuel.

14. The sensor circuit of claim 13 wherein said circuit means is an oscillator for sourcing a current, I, to said first and second capacitors and then sinking a current, I, therefrom as said first and second capacitors are charged and discharged between said first and second voltage levels respectively.

15. The sensor circuit of claims 13 or 14 wherein said detector circuit means includes:
a full wave rectifier circuit which is responsive to said current flowing through said second capacitor for providing a rectified current at an output thereof that is directly proportional to the magnitude of said current;
current mirror means having an output coupled to said output of said full wave rectifier circuit for sinking a said current of predetermined magnitude at said output thereof; and
comparator means having an input coupled to said outputs of said full wave rectifier circuit and said current mirror means and having an output, said comparator means being responsive to said magnitude of said rectified current becoming less than the magnitude of said current of predetermined magnitude for causing the output thereof to switch from a first output level to a second output level.

16. The sensor circuit of claim 15 including:
filter means coupled to the output of said comparator means for inhibiting switching transient signals; and output circuit means coupled to an output of said filter means which is responsive to said comparator means output switching to said second output level for producing an output signal therefrom which is indicative of an excessive amount of water content in the fuel a predetermined time interval after the output of said comparator means switches to said second output level.

17. A method for sensing a change in the capacitive value of a variable capacitor comprising the steps of:
connecting a capacitor of constant value in essentially parallel with the variable capacitor;
alternately charging and discharging both said variable capacitor and said constant value capacitor linearly between first and second voltage levels;
detecting the absolute magnitude of the current flowing through said constant value capacitor; and
comparing said detected current to a current of known magnitude wherein the difference current therebetween is indicative of the capacitive value of the variable capacitor.

18. A circuit for sensing the change in capacitance of a first capacitor, comprising:
a second capacitor of fixed value;
means coupled at a first circuit node to the first and said second capacitors for both linearly charging and discharging the same between first and second potential levels; and
detector means effectively placing said second capacitor and the first capacitor in parallel with respect to each other for detecting the difference in currents flowing in the first and said second capacitor.

19. The circuit of claim 18 wherein said detector means includes:
a first full wave rectifier circuit having an input and an output, said input being coupled to said second capacitor, said first full wave rectifier circuit providing a rectified current signal at said output that is proportional to a current sourced to or from said input through said second capacitor;
a second full wave rectifier circuit having an input and an output, said input being coupled to said first capacitor, said second full wave rectifier circuit providing a rectified current signal at said output that is proportional to a current sourced to or from said input through said first capacitors; and
a current mirror circuit having an input and an output, said input being coupled to said output of said first full wave rectifier circuit, said output being coupled to said output of said second full wave rectifier circuit, said current mirror circuit producing a current at said output that is proportional to said rectified current sourced from said input thereof.

20. The circuit of claim 19 wherein:
the first capacitor is coupled between said first circuit node and said input of said second full wave rectifier circuits; and
said second capacitor is coupled between said first circuit node and said input of said first full wave rectifier circuit.

21. The circuit of claim 20 including comparator means having an input coupled to said output of said current mirror circuit and an output, the output level state of said comparator means being switched between first and second levels as the magnitude of said current produced at said output of said current mirror exceeds and then becomes less than magnitude of rectified current appearing at said output of said second full wave rectifier circuit.

22. A method for detecting a change in magnitude of impedance of a variable impedance element, comprising the steps of:
alternately sourcing and sinking a constant current at a first circuit node to which the variable impedance element is connected;
connecting a first impedance element of like impedance to the variable impedance element to said first circuit node; and
measuring the absolute magnitude of the current flowing through said first impedance element, said absolute magnitude of the current flowing through said first impedance element varying as the impedance of the variable impedance element varies.

* * * * *